(12) United States Patent
Lee et al.

(10) Patent No.: US 11,504,540 B2
(45) Date of Patent: Nov. 22, 2022

(54) DEFIBRILLATION SYSTEM FOR SELF-DRIVING VEHICLES

(71) Applicants: Hyundai Motor Company, Seoul (KR); Kia Motors Corporation, Seoul (KR)

(72) Inventors: Baek Hee Lee, Suwon-si (KR); Min Hyuk Kwak, Seoul (KR); Jong Hun Lee, Hwaseong-si (KR); Hyun Kyu Park, Hwaseong-si (KR); Yo Seob Lee, Incheon (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 250 days.

(21) Appl. No.: 17/008,945

(22) Filed: Sep. 1, 2020

(65) Prior Publication Data
US 2021/0069521 A1    Mar. 11, 2021

(30) Foreign Application Priority Data

Sep. 11, 2019    (KR) .................. 10-2019-0112551

(51) Int. Cl.
*A61N 1/39*        (2006.01)
*B60W 40/08*    (2012.01)
(Continued)

(52) U.S. Cl.
CPC ....... *A61N 1/39044* (2017.08); *A61H 31/006* (2013.01); *A61N 1/3925* (2013.01); *B60N 2/002* (2013.01); *B60N 2/0232* (2013.01); *B60N 2/10* (2013.01); *B60N 2/16* (2013.01); *B60R 11/00* (2013.01); *B60R 13/08* (2013.01);
(Continued)

(58) Field of Classification Search
None
See application file for complete search history.

(56) References Cited

U.S. PATENT DOCUMENTS

2015/0224329 A1\* 8/2015 Wu .................. B60N 2/879
  297/183.1
2018/0348759 A1\* 12/2018 Freeman ............ A61B 5/021
(Continued)

FOREIGN PATENT DOCUMENTS

KR    10-2007-0053560 A    5/2007

*Primary Examiner* — Lail A Kleinman
(74) *Attorney, Agent, or Firm* — Morgan, Lewis & Bockius LLP

(57) ABSTRACT

A defibrillation system may include a cardiac arrest detector detecting whether cardiac arrest of a passenger has occurred in a state of taking a seat of a self-driving vehicle and fastening a seatbelt of the vehicle; a passenger posture detection device detecting a posture of the passenger; a seat driving device changing the posture of the passenger into another posture in which the passenger lies down based on a detection signal of the passenger posture detection device when the cardiac arrest of the passenger occurs; a heart position detector configured to search for a position of a heart of the passenger; a defibrillation robot to perform a CPR method or a method using an AED on the heart of the passenger; and a controller controlling operation of the seat driving device, the heart position detector, and the defibrillation robot based on detection signals of the cardiac arrest detector and the passenger posture detection device.

16 Claims, 6 Drawing Sheets

(51) Int. Cl.
*B60N 2/00*        (2006.01)
*B60N 2/16*        (2006.01)
*B60N 2/02*        (2006.01)
*B60N 2/10*        (2006.01)
*B60R 11/00*       (2006.01)
*B60R 13/08*       (2006.01)
*A61H 31/00*       (2006.01)
*B60W 60/00*       (2020.01)
*H04N 5/225*       (2006.01)

(52) U.S. Cl.
CPC ........ *B60W 40/08* (2013.01); *B60W 60/0016* (2020.02); *A61H 2201/10* (2013.01); *A61H 2201/5071* (2013.01); *A61H 2201/5092* (2013.01); *A61H 2230/045* (2013.01); *A61H 2230/405* (2013.01); *A61H 2230/625* (2013.01); *B60R 2011/0007* (2013.01); *B60R 2011/0015* (2013.01); *B60R 2011/0028* (2013.01); *B60R 2011/0029* (2013.01); *B60W 2420/42* (2013.01); *B60W 2540/221* (2020.02); *B60W 2540/223* (2020.02); *H04N 5/2253* (2013.01)

(56) References Cited

U.S. PATENT DOCUMENTS

| | | | |
|---|---|---|---|
| 2019/0266472 A1* | 8/2019 | Johnson | B64D 11/06 |
| 2020/0353934 A1* | 11/2020 | Vulcu | A61B 5/165 |
| 2021/0016686 A1* | 1/2021 | Yetukuri | B60N 2/5621 |

* cited by examiner

FIG. 9

| SHOCKABLE RHYTHM | VENTRICULAR TACHYCARDIA | | AED |
| --- | --- | --- | --- |
| | VENTRICULAR FIBRILLATION | | AED |
| NONSHOCKABLE RHYTHM | ASYSTOLE | | CPR |
| | PULSELESS ELECTRICAL ACTIVITIES | | CPR |

DEFIBRILLATION SYSTEM FOR SELF-DRIVING VEHICLES

CROSS-REFERENCE TO RELATED APPLICATION

The present application claims priority to Korean Patent Application No. 10-2019-0112551 filed on Sep. 11, 2019, the entire contents of which is incorporated herein for all purposes by this reference.

BACKGROUND OF THE INVENTION

Field of the Invention

The present invention relates to a defibrillation system for self-driving vehicles, and more particularly to a defibrillation system for self-driving vehicles capable of automatically performing defibrillation when cardiac arrest of a passenger sitting on a seat in a self-driving vehicle occurs.

Description of Related Art

A self-driving vehicle, which will be brought out in the future, is a vehicle capable of automatically traveling from a departure point to a designated destination without intervention of a driver or a passenger while recognizing the state of the vehicle and the environment around the vehicle.

Since no manipulation is required for the self-driving vehicle, an old weak person, a disabled person, and a person with diminished capacity may enter the self-driving vehicle for themselves as long as a desired destination is input.

In the case in which the old weak person or the person with diminished capacity enters the self-driving vehicle, however, abrupt cardiac arrest may occur. For the present reason, the self-driving vehicle, which will be brought out in the future, may be provided with a separate defibrillation apparatus of old weak people or people with diminished capacity.

In general, a cardio-pulmonary resuscitation (CPR) method and a method using an automated external defibrillator (AED) are used as defibrillation methods.

As is well known, the CPR method is a method of performing the functions of the heart and the lungs as a substitute when the lungs malfunction, wherein the heartbeat and breathing are checked and then chest pressing is repeatedly performed several tens of times and artificial respiration is repeatedly performed several times, and the method using the AED is a method of automatically analyzing the rhythm of the heart of a patient and applying electrical impact to the heart, if necessary, when an AED pad is attached around the heart, recovering the function of the heart.

Therefore, it is necessary for the self-driving vehicle, which will be brought out in the future, to be provided with a defibrillation apparatus configured for performing the CPR method, the method using the AED, or both the CPR method and the method using the AED The information included in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing a defibrillation system for self-driving vehicles configured such that, upon detecting whether cardiac arrest of a passenger sitting on a seat of a self-driving vehicle has occurred during traveling of the self-driving vehicle and determining that abrupt cardiac arrest has occurred, the seat is driven such that the passenger lies down facing upwards, an upper garment of the passenger is cut off by a defibrillation robot mounted around the seat, and a CPR method or a method using an AED is performed, whereby it is possible to easily prevent unexpected death and secondary incidents of the passenger during traveling of the self-driving vehicle.

The objects of the present invention are not limited to those described above. The objects of the present invention will be clearly understood from the following description and could be implemented by means defined in the claims and a combination thereof.

Various aspects of the present invention are directed to providing a defibrillation system for self-driving vehicles, the defibrillation system including a cardiac arrest detector configured to detect whether cardiac arrest of a passenger has occurred in the state of taking a seat of a self-driving vehicle and fastening a seatbelt, a passenger posture detection device configured to detect the posture of the passenger sitting on the seat, a seat driving device configured to change the posture of the passenger into another posture in which the passenger lies down based on a detection signal of the passenger posture detection device when the cardiac arrest of the passenger occurs, a heart position detector mounted around the seat to search for the position of a heart of the passenger lying down, a defibrillation robot mounted around the seat to perform a CPR method or a method using an AED on the heart of the passenger lying down, and a controller configured to control operation of the seat driving device, the heart position detector, and the defibrillation robot based on detection signals of the cardiac arrest detector and the passenger posture detection device.

The cardiac arrest detector may include one or more selected among a heartbeat sensing radar mounted to the surface of a ceiling in the self-driving vehicle to measure the heart rate of the passenger, an electrocardiogram sensor mounted in a seat back of the seat to measure the heart rate of the passenger, and an infrared heartbeat sensor mounted to a predetermined position of the seat back of the seat.

The passenger posture detection device may include a plurality of body pressure sensors mounted in the seat back and a seat cushion of the seat and a motion sensing camera mounted to the surface of the ceiling in the self-driving vehicle to detect the posture of the passenger sitting on the seat.

The seat driving device may include a plurality of air cells mounted in the seat back and the seat cushion of the seat in a symmetrical fashion to be expandable or contractible, a height adjustment unit configured to adjust the height of the front end portion of the seat cushion, a bolster driving unit configured to rotate bolsters of the seat back and the seat cushion, and an electric-powered recliner mounted between the rear end portion of the seat back and the lower end portion of the seat cushion to adjust a tilt angle of the seat cushion.

The height adjustment unit may include a first cylinder connected between the lower surface of the front end portion of the seat cushion and a seat rail to raise the front end portion of the seat cushion.

The bolster driving unit may include a bolster frame hinged to a seat frame in each of the seat back and the seat cushion to be rotatably located in each bolster and a second cylinder connected between the seat frame and the bolster frame to rotate the bolster frame.

The heart position detector may include an X-ray camera mounted to a predetermined position on the ceiling in the self-driving vehicle to capture an image of an upper body of the passenger sitting on the seat.

An X-ray shielding cover may be attached to the surface of the seat.

The defibrillation robot may include a multi-articulated arm having three or more arms interconnected via ball joints, a head rotatably mounted to a free end portion of the multi-articulated arm, a CPR pressure pad mounted to one end portion of the head, and an AED pad detachably attached to the circumference of the head.

A cutter configured to cut off an upper garment of the passenger may be mounted to the other end portion of the head.

An elastic roller, to which a touch sensor and a load cell are attached, may be rotatably mounted to a tip end portion of the cutter.

The defibrillation robot may be disposed at one of a floor panel around the seat, the surface of the ceiling above the seat, a front seat console around a front seat, a rear seat console around a rear seat, and the side surface of the seat back.

A powered seatbelt configured to be pulled according to a signal of the controller when the cardiac arrest of the passenger occurs may be adopted as a seatbelt configured to be fastened by the passenger sitting on the seat.

A carbon dioxide sensor configured to sense exhalation of the passenger may be mounted to one side of a headrest of the seat.

An oxygen supply nozzle configured to spray oxygen toward the mouth or nose of the passenger may be mounted to the other side of the headrest of the seat.

An oxygen tank configured to supply the oxygen to the oxygen supply nozzle may be mounted in the seat back of the seat.

Other aspects and exemplary embodiments of the present invention are discussed infra.

It is understood that the term "vehicle" or "vehicular" or other similar term as used herein is inclusive of motor vehicles in general such as passenger vehicles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

The above and other features of the present invention are discussed infra.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 9 is a table showing examples in which a method using an AED or a CPR method is performed by the defibrillation robot, which is a component of the defibrillation system for self-driving vehicles according to various exemplary embodiments of the present invention.

Figure 1:
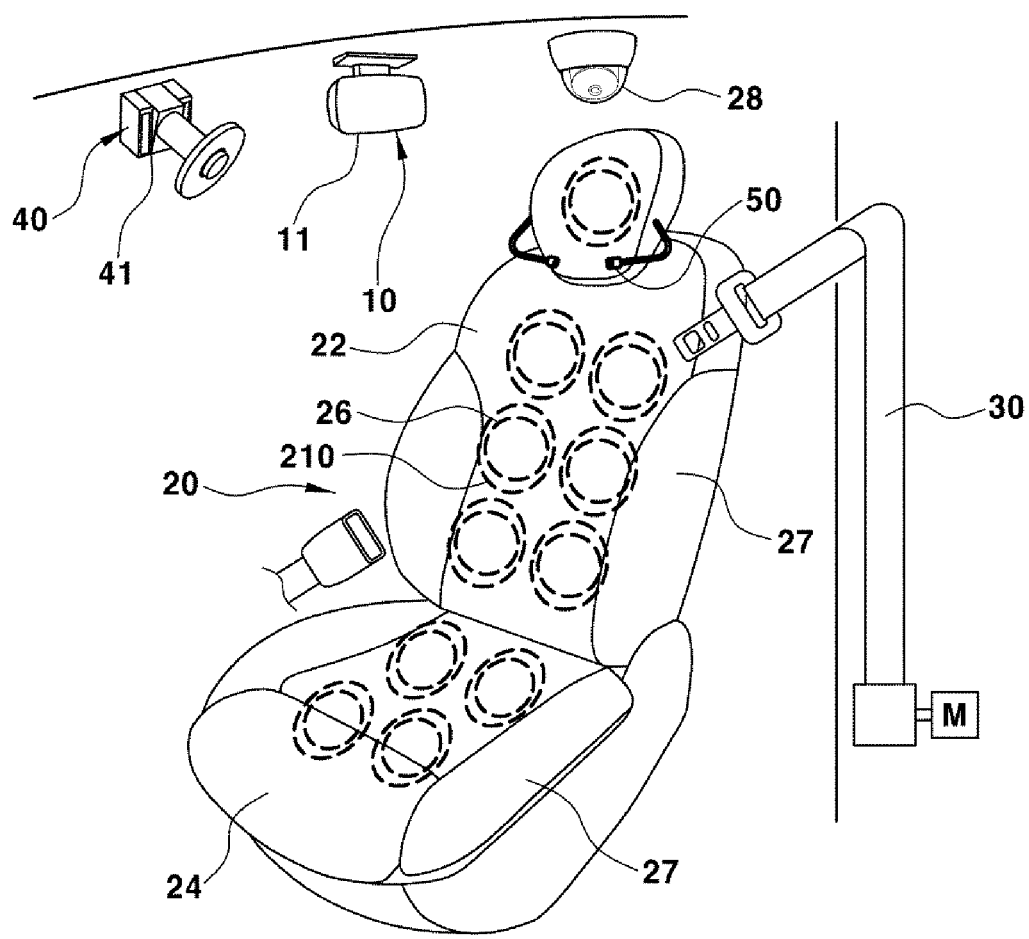
FIG. 1 is a schematic view showing the construction of a defibrillation system for self-driving vehicles according to various exemplary embodiments of the present invention.

It may be understood that the appended drawings are not necessarily to scale, presenting a somewhat simplified representation of various exemplary features illustrative of the basic principles of the present invention. The specific design features of the present invention as included herein, including, for example, specific dimensions, orientations, locations, and shapes, will be determined in part by the particular intended application and use environment.

In the figures, reference numbers refer to the same or equivalent portions of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Reference will now be made in detail to various embodiments of the present invention, examples of which are illustrated in the accompanying drawings and described below.

Figure 10:
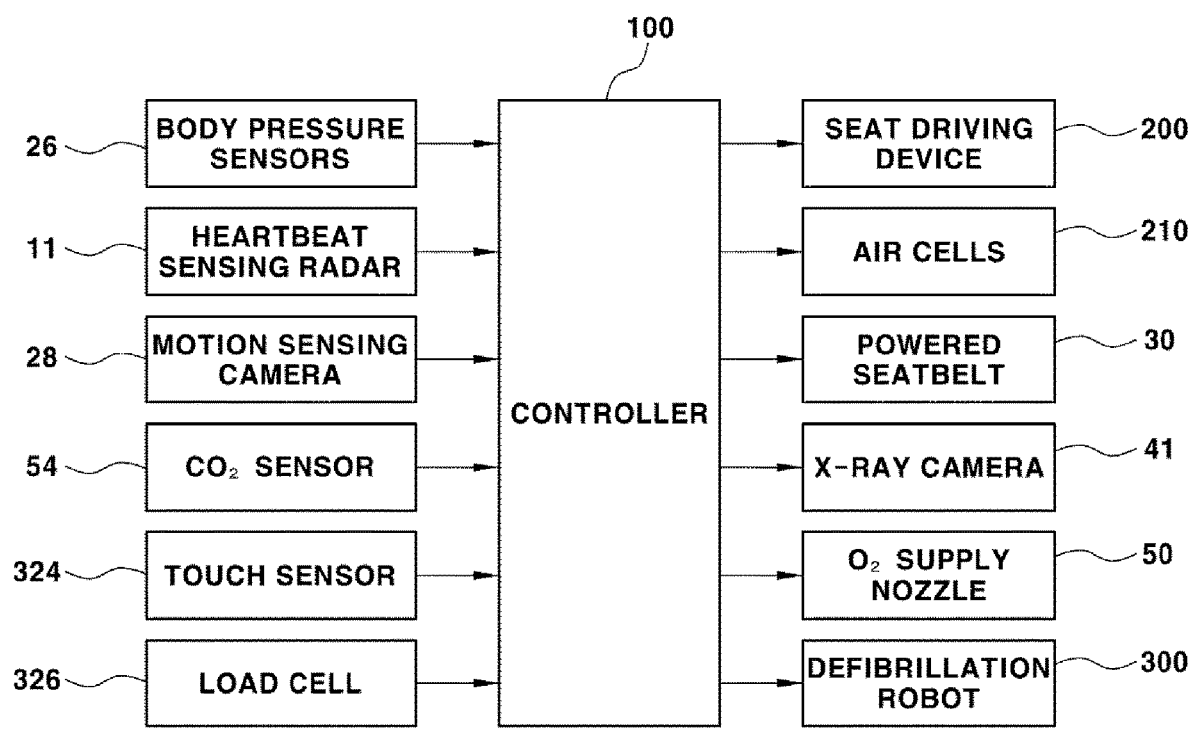
FIG. 10 is a view showing the control construction of the defibrillation system for self-driving vehicles according to various exemplary embodiments of the present invention.

FIG. 1 is a schematic view showing the construction of a defibrillation system for self-driving vehicles according to various exemplary embodiments of the present invention, and FIG. 10 is a view showing the control construction of the defibrillation system for self-driving vehicles according to various exemplary embodiments of the present invention, wherein reference numeral 10 indicates a cardiac arrest detector.

The cardiac arrest detector 10 detects whether cardiac arrest of a passenger has occurred in the state of taking a seat of a self-driving vehicle and fastening a seatbelt.

A self-driving vehicle, which will be brought out in the future, automatically travels to a destination without any manipulation as long as the destination is input. Consequently, an old weak person, a disabled person, and a person with diminished capacity may enter the self-driving vehicle. However, abrupt cardiac arrest may easily occur in consideration of mental and physical states.

When a passenger, such as an old weak person, a disabled person, or a person with diminished capacity, enters the self-driving vehicle and sits on a seat, therefore, a message alarm requesting that the passenger take a seat after taking off a coat for defibrillation when cardiac arrest occurs and an alarm requesting the passenger to fasten a seatbelt may be output through a speaker.

Preferably, to detect whether cardiac arrest of a passenger has occurred, the cardiac arrest detector 10 includes one or more selected among a heartbeat sensing radar mounted to the surface of the ceiling in the self-driving vehicle to measure the heart rate of a passenger, an electrocardiogram sensor mounted in a seat back of a seat to measure the heart rate of the passenger, and an infrared heartbeat sensor mounted to a predetermined position of the seat back of the seat.

The heartbeat sensing radar 11, which forms the cardiac arrest detector 10 and is mounted to the surface of the ceiling in the self-driving vehicle, monitors the heartbeat state (arrhythmia, ventricular fibrillation, or ventricular tachycardia) using motion of the heart and lungs of the passenger in the state of not being in contact with the passenger, and outputs a normal or abnormal heartbeat waveform to a controller.

Figure 8:
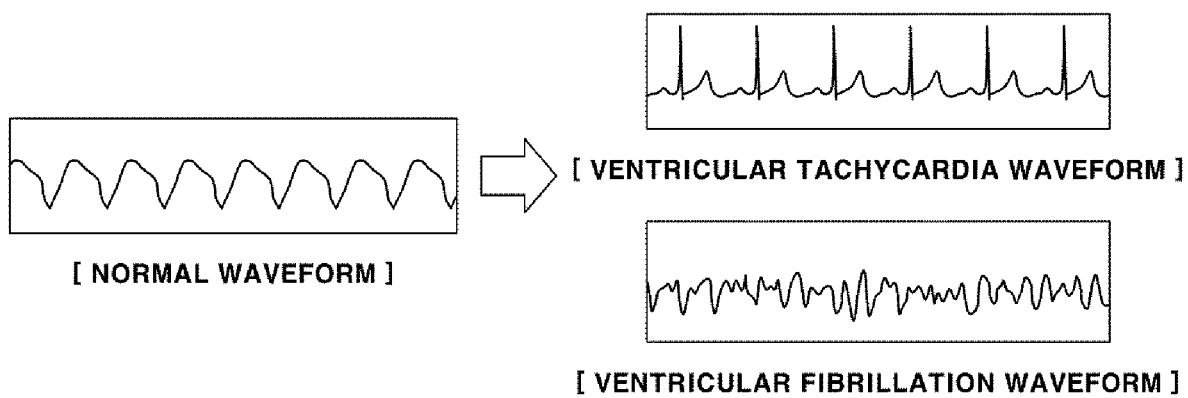
FIG. 8 is a view showing a heartbeat waveform detected by a radar sensor, which is a component of the defibrillation system for self-driving vehicles according to various exemplary embodiments of the present invention.

For example, as shown in FIG. 8, the heartbeat sensing radar 11 outputs a normal waveform in a normal heartbeat state, and outputs a ventricular tachycardia waveform or a ventricular fibrillation waveform in an abnormal heartbeat state, which causes cardiac arrest.

Upon receiving the ventricular tachycardia waveform or the ventricular fibrillation waveform from the heartbeat sensing radar 11, therefore, the controller 100 determines that the current state is a cardiac arrest state.

At the present time, to more clearly confirm the cardiac arrest state of the passenger, the posture of the passenger who sits on the seat is detected by a passenger posture detection device, and the result of detection is transmitted to the controller 100.

The passenger posture detection device may include a plurality of body pressure sensors 26 mounted in a seat back 22 and a seat cushion 24 of a seat 20 and a motion sensing camera 28 mounted to the surface of the ceiling in the self-driving vehicle to detect the posture of the passenger who sits on the seat.

The body pressure sensors 26 are mounted in the seat back 22 and the seat cushion 24 in a symmetrical fashion, and the motion sensing camera 28 is mounted to the surface of the ceiling above the seat on which the passenger sits.

When cardiac arrest of the passenger sitting on the seat has occurred in the state of fastening the seatbelt, the passenger falls unconscious, and the whole body of the passenger leans to one side while the upper body of the passenger is bent forwards.

At the present time, the body pressure of the passenger detected by the body pressure sensors 26 and a signal (an image signal) indicating the posture of the passenger who sits on the seat detected by the motion sensing camera 28 are received by the controller 100. In the case in which left and right components of the body pressure are imbalanced and the posture of the passenger who sits on the seat is a posture in which the passenger leans to one side while being bent forwards, the controller 100 may determine that the current state is a cardiac arrest state.

In conclusion, the controller 100 receives the ventricular tachycardia waveform or the ventricular fibrillation waveform from the heartbeat sensing radar 11, and in the case in which left and right components of the body pressure, received from the body pressure sensors 26, are imbalanced and the posture of the passenger who sits on the seat is confirmed to be a posture in which the passenger leans to one side while being bent forwards based on the image signal received from the motion sensing camera 28, the controller 100 determines that the current state is a cardiac arrest state.

Upon determining that cardiac arrest of the passenger has occurred, as described above, the controller 100 applies an operation signal to a well-known powered seatbelt 30 that the passenger is fastening to prevent the passenger from being further bent forwards or further leaning to one side thereof.

For reference, the powered seatbelt 30 is a predetermined seatbelt pulling device that rotates a drum of a retractor, in which the seatbelt is stored in the state of being wound, using motor driving force in the direction in which the seatbelt is pulled according to a signal of the controller such that the seatbelt is pulled.

It is possible to prevent the passenger from being further bent forwards or further leaning to one side through the pulling operation of the powered seatbelt 30.

Subsequently, the controller 100 applies a driving signal to a seat driving device 200 to change the posture of the passenger into a posture in which defibrillation may be easily performed.

The seat driving device 200 is configured to change the posture of the passenger sitting on the seat into a posture in which the passenger lies down facing upwards to easily perform defibrillation when cardiac arrest of the passenger occurs, and includes a plurality of air cells 210 configured to be operated according to a driving signal of the controller 100, a height adjustment unit 220, a bolster driving unit 230, and an electric-powered recliner 240.

First, the controller 100 drives the electric-powered recliner 240 to perform reclining such that the seat back 22 is maximally laid rearwards, whereby the upper body of the passenger bent forwards is unbent rearwards and thus a posture in which the passenger lies down is realized.

Furthermore, the front end portion of the seat back 22 is raised by the height adjustment unit 220 to realize a posture in which the passenger lies downwards.

Figure 2:
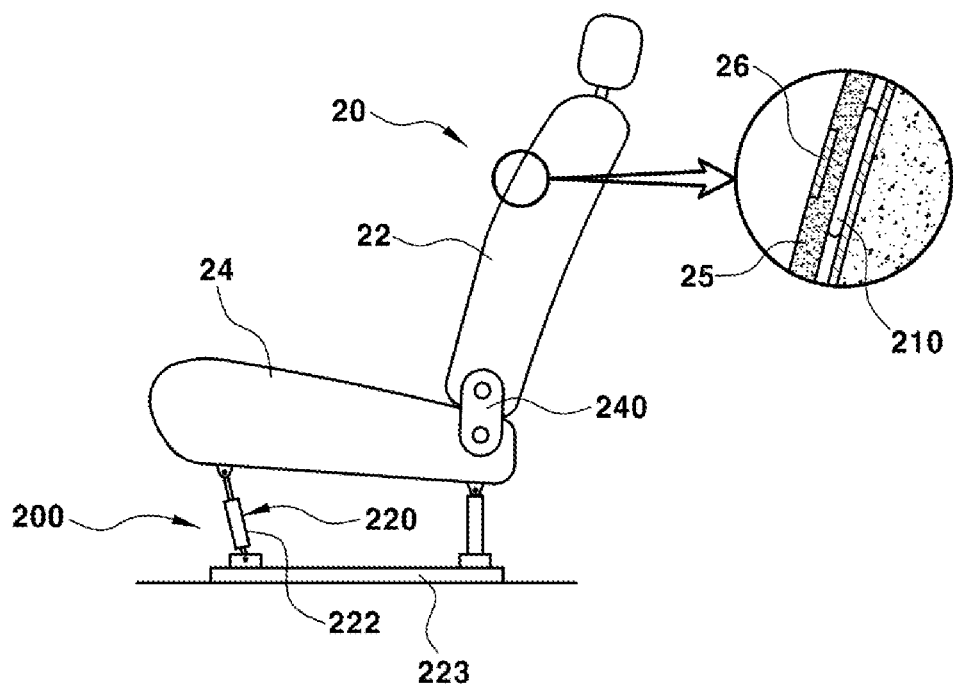
FIG. 2 and FIG. 3 are sectional views showing the structure of a seat of the defibrillation system for self-driving vehicles according to various exemplary embodiments of the present invention.

To this end, as shown in FIG. 2, the height adjustment unit 220 may include a first pneumatic or hydraulic cylinder 222 connected between the lower surface of the front end portion of the seat cushion 24 and a seat rail 223 to raise the front end portion of the seat cushion 24.

Consequently, the seat back 22 is maximally laid rearwards by driving of the electric-powered recliner 240, whereby the upper body of the passenger bent forwards is unbent rearwards, and at the same time the front end portion of the seat cushion 24 is raised by upward movement of a piston in the first pneumatic or hydraulic cylinder 222 of the height adjustment unit 220, whereby the thighs of the passenger are raised. Consequently, a posture in which the cardiac arrest passenger lies down is easily realized.

Even in the case in which the posture in which the passenger lies down is realized by reclining of the electric-powered recliner 240 and driving of the height adjustment unit 220, however, the body of the passenger leans to one side thereof. Consequently, it is necessary to lay the passenger down facing upwards for defibrillation.

To lay the passenger down facing upwards for defibrillation, the air cells 210 are expanded and contracted, and bolsters are expanded or contracted by driving of the bolster driving unit 230.

The air cells 210 are mounted in the seat back 22 and the seat cushion 24 of the seat in a symmetrical fashion to be expandable or contractible.

As shown in FIG. 2, the air cells 210 are disposed in the state in which a foam pad 25 is located between the air cells 210 and the body pressure sensors 26, which are disposed inside a seat cover, and are expanded by air supplied from an air supply means (e.g., an air pump) configured to be driven according to a driving signal of the controller 100.

Preferably, since, when the body of the cardiac arrest passenger leans to one side, body pressure values detected by the body pressure sensors 26 that contact with the body of the passenger are high and body pressure values detected by the body pressure sensors 26 that hardly contact with the body of the passenger are low, the air cells 210 behind the body pressure sensors 26 by which high body pressure values are detected are expanded and the air cells 210 behind the body pressure sensors 26 by which low body pressure values are detected are contracted in consideration of the difference between the body pressure values.

Figure 4:
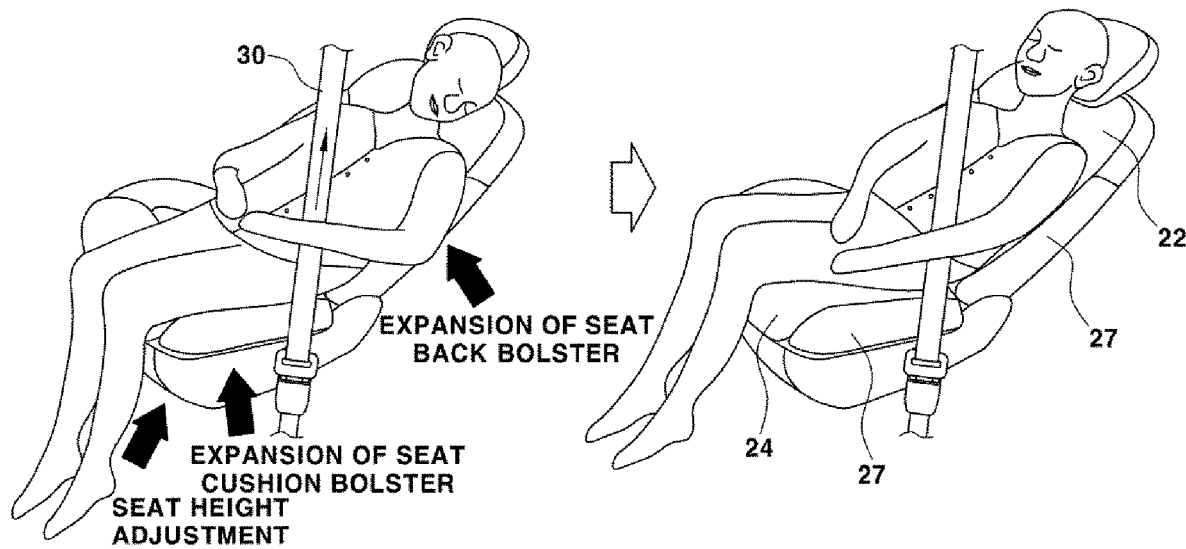
FIG. 4 is a schematic view showing the state in which the seat of the defibrillation system for self-driving vehicles according to various exemplary embodiments of the present invention is operated to lay a cardiac arrest passenger down facing upwards.

The body of the passenger leaning to one side is raised by expansion of the air cells 210, whereby the posture in which the passenger lies down obliquely may be changed into a posture in which the passenger lies down facing upwards, as shown in FIG. 4.

Also, in the case in which the passenger lies downs obliquely while the body of the passenger leans to one side, a portion of the body may come into tight contact with one of the bolsters of the seat back or the seat cushion (the bolster located at the side at which high body pressure is sensed), and therefore the controller 100 applies a driving signal to the bolster driving unit 230 to expand the bolster located at the side at which high body pressure is sensed.

Figure 3:
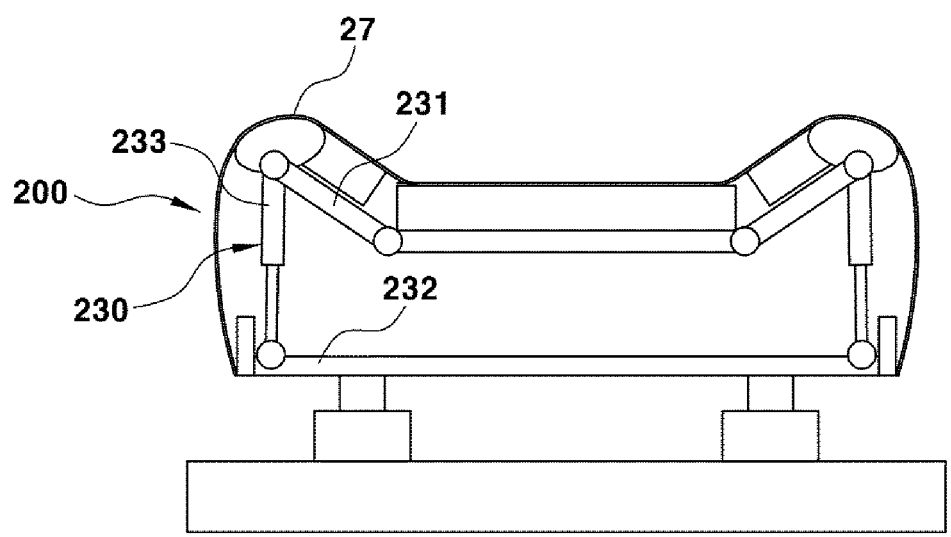

As shown in FIG. 3, the bolster driving unit 230 includes a bolster frame 231 hinged to a seat frame 232 in each of the seat back and the seat cushion to be rotatably located in each bolster 27 and a second pneumatic or hydraulic cylinder 233 connected between the seat frame 232 and the bolster frame 231 to rotate the bolster frame 231 while pushing or pulling the bolster frame 231.

When a piston in the second pneumatic or hydraulic cylinder 233 is moved forwards according to a control signal of the controller 100, the bolster frame 231 is rotated in an inward direction thereof, and at the same time the bolster located at the side at which high body pressure is detected is rotated in the same direction to push the body of the passenger, whereby the posture in which the passenger lies down obliquely may be changed into a posture in which the passenger lies down facing upwards.

As described above, the posture in which the passenger lies down obliquely may be changed into a posture in which the passenger lies down facing upwards for easy defibrillation by expansion and contraction of the air cells 210 and rotation of the bolster by the bolster driving unit 230, as shown in FIG. 4.

Next, upon confirming that the posture of the passenger is a posture in which the passenger lies down facing upwards based on the image signal received from the motion sensing camera and that the body pressure values detected by the body pressure sensors are within a predetermined range, the controller 100 issues a command signal for searching for the position of a heart to a heart position detector 40 as a preliminary procedure for defibrillation.

The heart position detector 40 may include an X-ray camera 41 mounted to a predetermined position on the ceiling in the self-driving vehicle to capture an image of the upper body of the passenger sitting on the seat.

When the X-ray camera 41 captures an image of ribs around the heart, an image of a frame structure in the seat may also be captured. For the present reason, a separate X-ray shielding cover is attached to the surface of the seat 20.

The X-ray camera 41 captures an image of the ribs around the heart, and at the same time transmits information related to the position and coordinates of the heart spaced away from the ribs with a predetermined distance to the controller 100.

The controller 100 transmits the information related to the position and coordinates of the heart to a defibrillation robot 300, and issues a command signal for performing defibrillation to the defibrillation robot 300.

The defibrillation robot 300 is configured to perform a CPR method or a method using an AED on the heart of the passenger who lies down facing upwards in the state of sitting on the seat, and may be disposed at one of a floor panel around the seat, the surface of the ceiling above the seat, a front seat console around a front seat, a rear seat console around a rear seat, and the side surface of the seat back.

Figure 5:
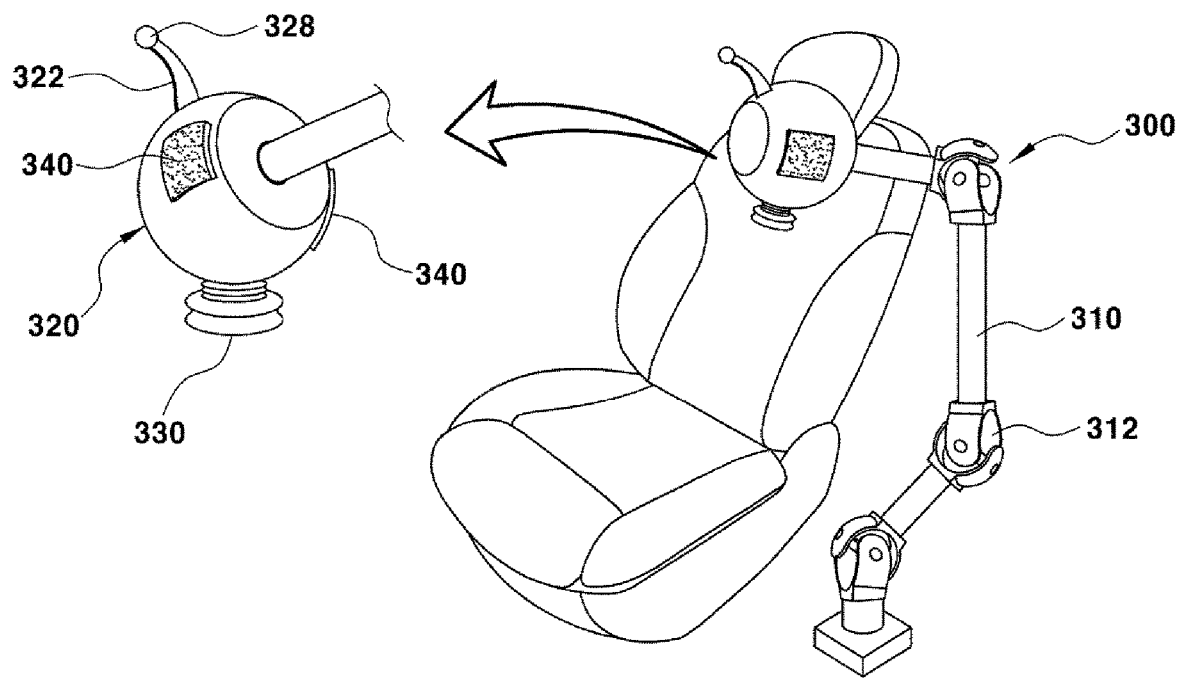
FIG. 5 is a schematic view showing a defibrillation robot, which is a component of the defibrillation system for self-driving vehicles according to various exemplary embodiments of the present invention.

As shown in FIG. 5, the defibrillation robot 300 includes a multi-articulated arm 310 having three or more arms interconnected via ball joints 312, a head 320 rotatably mounted to a free end portion of the multi-articulated arm 310, a rubber-made CPR pressure pad 330 mounted to one end portion of the head 320, and a pair of AED pads 340 detachably attached to the circumference of the head 320.

Furthermore, a cutter 322 for cutting off an upper garment to perform CPR on the heart of the passenger or to attach the AED pads 340 to the skin of the passenger around the heart is mounted to the other end portion of the head 320.

An elastic roller 328, to which a touch sensor 324 and a load cell 326 are attached, is rotatably mounted to a tip end portion (a portion that contacts with the skin) of the cutter 322 to prevent the skin from being damaged by the cutter 322.

Figure 6:
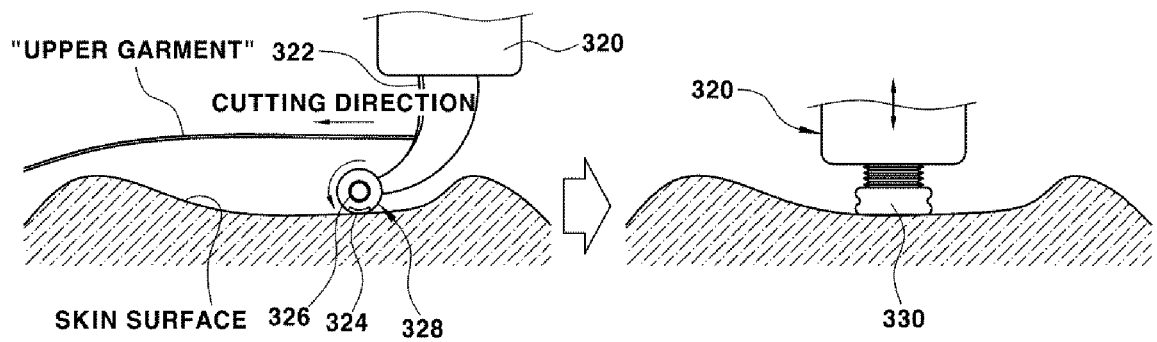
FIG. 6 is a schematic view showing the operation state of the defibrillation robot, which is a component of the defibrillation system for self-driving vehicles according to various exemplary embodiments of the present invention.

When the defibrillation robot 300 receives a defibrillation execution command signal of the controller 100, the multi-articulated arm 310 of the defibrillation robot 300 is moved to the heart of the passenger, the head 320 is rotated such that the elastic roller 328, mounted to the tip end portion of the cutter 322, contacts with the skin, as shown in FIG. 6, and the cutter 322 cuts off an upper garment of the passenger according to the rectilinear movement of the multi-articulated arm 310.

When the elastic roller 328, mounted to the tip end portion of the cutter 322, contacts with the skin, the touch sensor 324 detects contact with the skin, and at the same time the load cell 326 detects skin contact pressure within a reference pressure range. The results of detecting are transmitted to the controller 100. The controller 100 issues a command for stopping downward movement of the head 320 to the defibrillation robot 300. As a result, the cutter 322 does not directly contact with the skin, whereby it is possible to prevent the skin from being damaged by the cutter 322.

Subsequently, the controller 100 issues a command for rectilinear movement of the head 320 to the defibrillation robot 300, and the head 320 performs rectilinear movement, and at the same time the cutter 322 cuts off the upper garment and buttons such that the portion of the skin above and around the heart is exposed outside.

Subsequently, the controller 100 determines whether to perform a CPR method or a method using the AED, each of which is a defibrillation method.

Referring to FIG. 9, upon confirming that the heartbeat state of the passenger is a ventricular fibrillation or ventricular tachycardia state corresponding to AED facilitating rhythm based on information related to the heartbeat state of the passenger received from the heartbeat sensing radar 11, the controller 100 determines to use the method using the AED as the defibrillation method. On the other hand, upon confirming that the heartbeat state of the passenger is asystole or pulseless electrical activities, the controller 100 determines to use the CPR method as the defibrillation method.

Upon determining to use the method using the AED as the defibrillation method, the controller 100 issues a command signal for performing the method using the AED to the defibrillation robot 300.

For reference, the method using the AED is a defibrillation method in which a pair of AED pads, which are predetermined electric pads, is attached to a position under the right collarbone of a patient and a position around the armpit beside the left nipple of the patient, strong current is temporarily supplied to the heart via the AED pads such that the heart normally pulses again.

After the multi-articulated arm 310 of the defibrillation robot 300 is moved to the heart of the passenger, the head 320 is rotated, and at the same time the AED pads 340, attached to the circumference of the head 320, may be transferred and attached to the skin of the passenger.

Subsequently, current is supplied to the AED pads 340 using a power source, such as a battery, mounted in the defibrillation robot 300 such that heart defibrillation is automatically performed.

When the method using the AED is performed, oxygen is sprayed toward the mouth or nose of the passenger to supply oxygen to the passenger.

Figure 7:
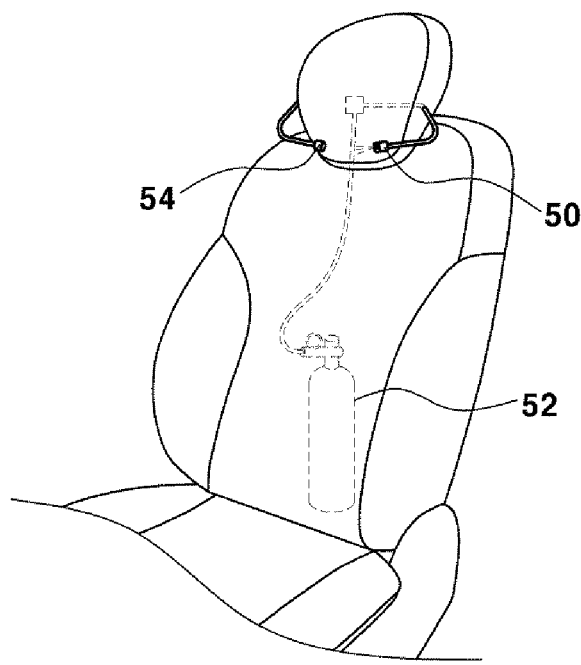
FIG. 7 is a schematic view showing an oxygen supplier, which is a component of the defibrillation system for self-driving vehicles according to various exemplary embodiments of the present invention.

To this end, as shown in FIG. 7, an oxygen supply nozzle 50 for spraying oxygen toward the mouth or nose of the passenger is mounted to one side of a headrest of the seat 20, and an oxygen tank 52 for supplying oxygen to the oxygen supply nozzle 50 is mounted in the seat back.

The controller 100 opens an electric-powered valve mounted to an inlet of the oxygen tank 52, whereby oxygen in the oxygen tank 52 may be sprayed toward the mouth or nose of the passenger through the oxygen supply nozzle 50.

Furthermore, a carbon dioxide sensor 54 for detecting exhalation of the passenger is mounted to the other side of the headrest of the seat 20. The controller 100 checks the exhalation of the passenger in real time based on a detecting signal of the carbon dioxide sensor 54.

When the heartbeat sensing radar 11 outputs the heartbeat state of the passenger as a normal waveform and the carbon dioxide sensor 54 detects exhalation of the passenger during the execution of the method using the AED, the controller 100 determines that the heartbeat state of the passenger returns to a normal state and issues an AED stop signal to the defibrillation robot 300, whereby the automatic defibrillation process is finished.

On the other hand, upon determining to use the CPR method as the defibrillation method, the controller 100 issues a command signal for performing the CPR method to the defibrillation robot 300.

After the multi-articulated arm 310 of the defibrillation robot 300 is moved to the heart of the passenger, the head 320 is rotated and at the same time is moved downwards such that the rubber-made CPR pressure pad 330, mounted to one end portion of the head 320, comes into tight contact with the heart of the passenger.

Subsequently, the multi-articulated arm 310 of the defibrillation robot 300 is reciprocated rectilinearly in the upward-downward direction within a predetermined distance such that the CPR pressure pad 330 repeatedly presses the chest of the passenger including the heart.

At the present time, the controller 100 opens the electric-powered valve mounted to the inlet of the oxygen tank 52, whereby oxygen in the oxygen tank 52 may be sprayed toward the mouth or nose of the passenger through the oxygen supply nozzle 50 such that artificial respiration is also achieved.

When the heartbeat sensing radar 11 outputs the heartbeat state of the passenger as a normal waveform and the carbon dioxide sensor 54 detects exhalation of the passenger during execution of the CPR method, the controller 100 determines that the heartbeat state of the passenger returns to a normal state and issues a CPR stop signal to the defibrillation robot 300, whereby the automatic defibrillation process is finished.

Meanwhile, upon determining that the passenger is in a cardiac arrest state based on a detecting signal of the heartbeat sensing radar 11, it is preferable for the controller 100 to automatically transmit an emergency rescue message or the current location to 911, a medical institution, a family member, and an acquaintance through a communication means in the vehicle such that the passenger may be urgently treated within a short time.

Furthermore, it is preferable for the controller 100 to stop or park the self-driving vehicle in a stable stopping or parking space through cooperation with a traveling control unit of the self-driving vehicle such that defibrillation may be performed and to inform outside or neighboring vehicles of the emergency by turning on an emergency lamp of the vehicle.

Furthermore, it is preferable for the controller 100 to automatically adjust the temperature and humidity in the vehicle to optimal temperature and humidity for the patient through cooperation with an air conditioner of the self-driving vehicle.

As described above, when abrupt cardiac arrest of the passenger sitting on the seat of the self-driving vehicle has occurred, the seat is driven such that the passenger lies down facing upwards, the upper garment of the passenger is cut off by the defibrillation robot disposed around the seat, and the CPR method or the method using the AED is performed, whereby it is possible to easily prevent unexpected death and secondary incidents of the passenger and to improve safety and quality of the self-driving vehicle.

As is apparent from the foregoing, the present invention may have the following effects.

First, when abrupt cardiac arrest of a passenger sitting on the seat of the self-driving vehicle has occurred, the seat is driven such that the passenger lies down facing upwards, an upper garment of the passenger is cut off by the defibrillation robot disposed around the seat, and the CPR method or the method using the AED is performed, whereby it is possible to easily prevent unexpected death and secondary incidents of the passenger.

Second, even when an old weak person, a disabled person, and a person with limited capacity enter the self-driving vehicle, the defibrillation process using the CPR method or the method using the AED is automatically performed, whereby it is possible to improve safety and quality of the self-driving vehicle.

Furthermore, the term "controller" refers to a hardware device including a memory and a processor configured to execute one or more steps interpreted as an algorithm structure. The memory stores algorithm steps, and the processor executes the algorithm steps to perform one or more processes of a method in accordance with various exemplary embodiments of the present invention. The controller according to exemplary embodiments of the present invention may be implemented through a nonvolatile memory configured to store algorithms for controlling operation of various components of a vehicle or data about software commands for executing the algorithms, and a processor configured to perform operation to be described above using the data stored in the memory. The memory and the processor may be individual chips. Alternatively, the memory and the processor may be integrated in a single chip. The processor may be implemented as one or more processors.

The controller may be at least one microprocessor operated by a predetermined program which may include a series of commands for carrying out a method in accordance with various exemplary embodiments of the present invention.

The aforementioned invention can also be embodied as computer readable codes on a computer readable recording medium. The computer readable recording medium is any data storage device that can store data which may be thereafter read by a computer system. Examples of the computer readable recording medium include hard disk drive (HDD), solid state disk (SSD), silicon disk drive (SDD), read-only memory (ROM), random-access memory (RAM), CD-ROMs, magnetic tapes, floppy discs, optical data storage devices, etc and implementation as carrier waves (e.g., transmission over the Internet).

For convenience in explanation and accurate definition in the appended claims, the terms "upper", "lower", "inner", "outer", "up", "down", "upwards", "downwards", "front", "rear", "back", "inside", "outside", "inwardly", "outwardly", "internal", "external", "inner", "outer", "forwards", and "backwards" are used to describe features of the exemplary embodiments with reference to the positions of such features as displayed in the figures. It will be further understood that the term "connect" or its derivatives refer both to direct and indirect connection.

Furthermore, the term of "fixedly connected" signifies that fixedly connected members always rotate at a same speed. Furthermore, the term of "selectively connectable" signifies "selectively connectable members rotate separately when the selectively connectable members are not engaged to each other, rotate at a same speed when the selectively connectable members are engaged to each other, and are stationary when at least one of the selectively connectable members is a stationary member and remaining selectively connectable members are engaged to the stationary member".

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A defibrillation system for a vehicle, the defibrillation system comprising:
    a cardiac arrest detector configured to detect whether cardiac arrest of a passenger has occurred in a state of the passenger's taking a seat of the vehicle and fastening a seatbelt of the vehicle and to generate a detection signal;
    a passenger posture detection device configured to detect a first posture of the passenger sitting on the seat;
    a seat driving device configured to change the posture of the passenger into a second posture in which the passenger lies down according to a detection signal of the passenger posture detection device when the cardiac arrest of the passenger occurs;
    a heart position detector mounted around the seat to search for a position of a heart of the passenger lying down;
    a defibrillation robot mounted around the seat to perform a cardio-pulmonary resuscitation (CPR) or a method using an automated external defibrillator (AED) on the heart of the passenger lying down; and
    a controller electrically connected to the cardiac arrest detector, the passenger posture detection device, the seat driving device, the heart position detector, and the defibrillation robot and configured to control operation of the seat driving device, the heart position detector, and the defibrillation robot according to the detection signals of the cardiac arrest detector and the passenger posture detection device.

2. The defibrillation system according to claim 1, wherein the cardiac arrest detector includes one or more selected from:
    a heartbeat sensing radar mounted to a surface of a ceiling in the vehicle to measure a heart rate of the passenger;
    an electrocardiogram sensor mounted in a seat back of the seat to measure the heart rate of the passenger; and
    an infrared heartbeat sensor mounted to a predetermined position of the seat back of the seat.

3. The defibrillation system according to claim 1, wherein the passenger posture detection device includes:
    a plurality of body pressure sensors mounted in a seat back and a seat cushion of the seat; and
    a motion sensing camera mounted to a surface of a ceiling in the vehicle to detect the first posture and the second posture of the passenger sitting on the seat.

4. The defibrillation system according to claim 1, wherein the seat driving device includes:
    a plurality of air cells symmetrically mounted in a seat back and a seat cushion of the seat to be expandable or contractible;
    a height adjustment unit engaged to the seat cushion and configured to adjust a height of a front end portion of the seat cushion;
    a bolster driving unit configured to rotate bolsters of the seat back and the seat cushion; and an electric-powered recliner mounted between a rear end portion of the seat back and a lower end portion of the seat cushion to adjust a tilt angle of the seat cushion.

5. The defibrillation system according to claim 4, wherein the height adjustment unit includes a first cylinder connected between a lower surface of the front end portion of the seat cushion and a seat rail to raise the front end portion of the seat cushion.

6. The defibrillation system according to claim 4, wherein the bolster driving unit includes:
 a bolster frame hinged to a seat frame in each of the seat back and the seat cushion to be rotatably located in each bolster; and
 a second cylinder connected between the seat frame and the bolster frame to rotate the bolster frame.

7. The defibrillation system according to claim 1, wherein the heart position detector includes an X-ray camera mounted to a predetermined position on a ceiling in the vehicle to capture an image of an upper body of the passenger sitting on the seat.

8. The defibrillation system according to claim 7, wherein an X-ray shielding cover is attached to a surface of the seat.

9. The defibrillation system according to claim 1, wherein the defibrillation robot includes:
 a multi-articulated arm having three or more arms interconnected via ball joints;
 a head rotatably mounted to a free end portion of the multi-articulated arm;
 a CPR pressure pad mounted to a first end portion of the head; and
 an AED pad detachably attached to a circumference of the head.

10. The defibrillation system according to claim 9, wherein a cutter configured to cut off an upper garment of the passenger is mounted to a second end portion of the head.

11. The defibrillation system according to claim 10, wherein an elastic roller, to which a touch sensor and a load cell are attached, is rotatably mounted to a tip end portion of the cutter.

12. The defibrillation system according to claim 9, wherein the defibrillation robot is mounted at one of a floor panel around the seat, a surface of a ceiling above the seat, a front seat console around a front seat, a rear seat console around a rear seat, and a side surface of a seat back.

13. The defibrillation system according to claim 1, wherein a powered seatbelt configured to be pulled according to a signal of the controller when the cardiac arrest of the passenger occurs is adopted as a seatbelt configured to be fastened by the passenger sitting on the seat.

14. The defibrillation system according to claim 1, wherein a carbon dioxide sensor configured to sense exhalation of the passenger is mounted to a first side of a headrest of the seat.

15. The defibrillation system according to claim 1, wherein an oxygen supply nozzle configured to spray oxygen toward a mouth or nose of the passenger is mounted to a second side of a headrest of the seat.

16. The defibrillation system according to claim 15, wherein an oxygen tank configured to supply the oxygen to the oxygen supply nozzle is mounted in a seat back of the seat.

* * * * *